(12) United States Patent
Bushberg et al.

(10) Patent No.: US 7,038,205 B2
(45) Date of Patent: May 2, 2006

(54) PROBE APPARATUS WITH LASER GUIDING FOR LOCATING A SOURCE OF RADIOACTIVITY

(75) Inventors: Jerrold T. Bushberg, Sacramento, CA (US); James P. Case, Dixon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/903,192

(22) Filed: Jul. 30, 2004

(65) Prior Publication Data
US 2006/0049351 A1    Mar. 9, 2006

Related U.S. Application Data

(60) Provisional application No. 60/571,417, filed on May 13, 2004.

(51) Int. Cl.
*G01T 1/169* (2006.01)
(52) U.S. Cl. .............................. 250/336.1; 250/515.1; 600/436
(58) Field of Classification Search ............. 250/336.1, 250/515.1; 600/436
See application file for complete search history.

(56) References Cited

U.S. PATENT DOCUMENTS

| | | | |
|---|---|---|---|
| 4,081,682 A * | 3/1978 | Ohlenschlager et al. | 250/362 |
| 4,200,803 A * | 4/1980 | Becker et al. | 378/148 |
| 5,204,533 A * | 4/1993 | Simonet | 250/361 R |
| 5,286,973 A * | 2/1994 | Westrom et al. | 250/253 |
| 5,475,219 A | 12/1995 | Olson | |
| 5,694,933 A | 12/1997 | Madden et al. | |
| 5,859,436 A * | 1/1999 | Harada et al. | 250/370.01 |
| 6,125,335 A * | 9/2000 | Simon et al. | 702/85 |
| 6,151,788 A * | 11/2000 | Cox et al. | 33/286 |
| 6,495,834 B1 * | 12/2002 | Corvo et al. | 250/363.1 |
| 6,563,120 B1 | 5/2003 | Baldwin et al. | |
| 6,643,538 B1 * | 11/2003 | Majewski et al. | 600/436 |
| 2002/0197025 A1 * | 12/2002 | Vaganov et al. | 385/92 |
| 2004/0141586 A1 * | 7/2004 | Hsieh et al. | 378/63 |
| 2004/0179647 A1 * | 9/2004 | Zhao et al. | 378/57 |

FOREIGN PATENT DOCUMENTS

JP        408275955 A    10/1996

OTHER PUBLICATIONS

Eurami Group Inc.; Gamma-Scout User Manual, Jul. 30, 1998, Cover pages, pp. 29-51.

(Continued)

*Primary Examiner*—Otilia Gabor
*Assistant Examiner*—Christine Sung
(74) *Attorney, Agent, or Firm*—John P. O'Banion

(57) ABSTRACT

A highly directional radiation probe with a laser guide to pinpoint the position of a source of radiation. The probe is configured with a lead pinhole collimator, a radiation detector configured to detect radiation through the pinhole, and a laser positioned in the collimator and configured to project a beam through the pinhole. When the probe is aligned with the radiation source detected through the pinhole, the laser is activated and projects a beam at the source position. The probe can scan a person in three dimensions to quickly locate radioactive shrapnel for removal. The probe can also be used to pinpoint small sources of radiation in a localized area within a radius up to about 20 meters or further, depending on the level of radiation exposure encountered. The probe is adapted to be hand-held, battery-operated and used with a visual or audible radioactivity indicator or a visual display device.

58 Claims, 9 Drawing Sheets

OTHER PUBLICATIONS

Bruker Daltonics; SVG 2, The New Generation of Nuclear Radiation Detectors, Downloaded from Internet, Date Unknown, pp. 1-2.

Exploranium Radiation Detection Systems; The Identifier, GR-135, Brochure, Date Unknown, pp. 1-4.

Exploranium Radiation Detection Systems; Gamma Radiation Dectector, GR-110G, Brochure, Date Unknown, pp. 1-2.

Automatic Measuring Systems for the Environment; GMM 78—Handheld Radiation Detector (Cracker), Downloaded from Internet Jan. 18, 2004, p. 2.

Raynger Minitemp MT Series, Brochure, Date Unknown, 1 pg.

Less EMF Inc.; The EMF Safety Superstore, IR, UV & Ionizing Radiation Detectors, 1996, Downloaded from Internet, pp. 1-9.

* cited by examiner

PROBE APPARATUS WITH LASER GUIDING FOR LOCATING A SOURCE OF RADIOACTIVITY

CROSS-REFERENCE TO RELATED APPLICATIONS

This application claims priority from U.S. provisional application Ser. No. 60/571,417 filed on May 13, 2004, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to devices for indicating the location of radioactive objects, and more particularly to a hand-held and automated wound probe with a laser guide to pinpoint radioactive objects in a body.

2. Description of Related Art

It is well known that ionizing radiation can be detected by Geiger Mueller Tubes (GMT) and other detectors. These devices are routinely used in medicine to detect radiopharmaceuticals injected in patients to locate abnormalities such as organ damage or cancer. Radiation detectors are also used in science and industry to identify and measure sources of radiation. Most radiation detectors are omni-directional and indicate radiation intensity and distance from a source by the detector's signal strength. The user must approach and wave the probe near the source to identify the general location.

An area of increasing concern is the detection and removal of high activity and high specific activity (HASA) radiation sources, such as radioactive shrapnel, embedded in a victim through accidental or intentional means. These HASA sources represent an acute exposure risk to the victim, emergency responders and medical personnel due to high levels of gamma radiation emitted. If not removed quickly, the victim may receive a debilitating or fatal dose of radiation in a relatively short amount of time. In some cases, the HASA source material may be very small or radiographic transparent to X-rays and other conventional shrapnel detection methods. Further, the level of radiation emitted from a HASA source would register off the scale and potentially damage radiation detection/imaging equipment available in a medical facility, rendering them ineffective for pinpointing the source.

Emergency responders and medical personnel are at risk of overexposure to radiation when in close proximity to victims with embedded HASA sources. In some radiological emergency situations, it would be appropriate to identify victims with HASA sources and separate them from other patients and medical personnel. It would be preferable if emergency responders and medical personnel could pinpoint HASA sources from a distance to manage exposure risk.

In an emergency surgical situation, a surgeon would need to find and remove the HASA source quickly. Without a quick and efficient method to pinpoint HASA sources, a victim would be subject to excess tissue debridement, trauma or amputation to ensure immediate removal of radioactive shrapnel from the body.

What is needed is a radiation probe to accurately detect and pinpoint a HASA radiation source embedded in a victim. A probe that is portable and would pinpoint a HASA radiation source from a relatively safe distance is preferable.

BRIEF SUMMARY OF THE INVENTION

One embodiment of the invention is a radiation probe for indicating a source of gamma radiation that comprises a lead collimator having proximal and distal ends, a pinhole positioned at the distal end of the collimator, a means for detecting radiation configured to detect gamma radiation and positioned adjacent the pinhole, wherein a highly directional radiation probe is formed, and a means for generating an observable beam positioned adjacent the pinhole and where the collimator and the means for generating an observable beam form a highly directional light emitter for visually locating a source of radioactivity.

Another aspect of the invention is a means for detecting radiation comprising at least one gamma ray detector.

A further aspect of the invention is a radiation probe with an Ion Chamber, a Geiger Mueller Tube, a Diode Based Detector, a Sodium Iodide detector or a Cesium Iodide detector.

A still further aspect of the invention is a means for generating an observable beam chosen from a diode laser, an Argon laser or a Helium Neon laser.

Another aspect of the invention is a radiation probe with a housing adapted to support the collimator.

A still further aspect of the invention is a radiation probe with a momentary switch configured to activate the means for generating an observable beam.

Another aspect of the invention is a battery pack configured to provide power to the means for generating an observable beam.

A still further aspect of the invention is a plurality of level indicators configured to indicate orientation of the radiation probe.

Another aspect of the invention is a radiation probe where the housing is constructed of aluminum.

A further aspect of the invention is a lead plug having a distal end and a proximal end where the distal end of the plug adapted to couple to the proximal end of the collimator and the proximal end of the plug is adapted to couple to the housing and where the plug is adapted to block gamma radiation to the means for detecting radiation.

A still further aspect of the invention is a pinhole in the collimator up to approximately 0.250 inches in diameter.

Another aspect of the invention is a removable sleeve adapted to change the cross section area of the pinhole.

A further aspect of the invention is a variable aperture mechanism adapted to change the diameter of the pinhole.

Another aspect of the invention is the collimator having a center core mounted in the probe and a cylindrical shell adapted to mate with the center core and further adapted to be removable from the probe. A still further aspect of the invention is a radiation probe adapted to to be coupled to a visual and/or audible indicator of radiation intensity.

Another aspect of the invention is a sleeve configured to mount in the collimator and support the means for detecting radiation and the means for generating an observable beam and adapted to align the means for generating an observable beam with the pinhole in the collimator.

Another embodiment of the invention is an articulating arm adapted to support the probe and perform a systematic scan, and a means for producing a visual image connected to the radiation detection means when a systematic scan is performed.

A further aspect of the invention is where the means for producing a visual image is a visual display device selected from the group consisting essentially of a printer, a plotter, a display screen and a stereotactic device.

A still further aspect of the invention is where the articulating arm is further adapted to articulate in three dimensions.

Another aspect of the invention is where the articulating arm is further adapted to articulate robotically.

Another embodiment of the invention is a probe with laser guiding for indicating a point source of radiation that comprises a lead collimator having proximal and distal ends, a pinhole in the distal end of the collimator, at least one gamma radiation detector positioned within the collimator and configured to detect gamma radiation passing through the pinhole and a laser emitter positioned in the collimator and aligned to project a beam through the pinhole in the collimator where the collimator and the gamma radiation detector form a highly directional radiation probe and where the laser emitter is configured to indicate a point source of gamma radiation detected to the gamma radiation detector.

A still further embodiment of the invention is a probe with laser guiding for indicating a point source of radiation embedded in a person comprised of a lead collimator having proximal and distal ends, a pinhole positioned at the distal end of the collimator, a gamma radiation detector positioned within the collimator, for detecting gamma radiation passing through the pinhole, where the collimator and the gamma radiation detector form a highly directional radiation probe, and a laser positioned in the collimator, aligned to project a beam through the pinhole in the collimator, and configured to indicate a point source of radiation detected by the radiation detector.

Another embodiment is a laser guiding radiation probe for indicating a source of gamma radiation that comprises a lead collimator having proximal and distal ends, a pinhole positioned in the distal end of the collimator, a means for detecting radiation positioned within the collimator and configured to detect gamma radiation passing through the pinhole, a computing device connected to the gamma radiation detector, configured to compare radiation intensity signals transmitted by the gamma radiation detector, configured to determine the radiation signal with the highest value from a set of radiation signals, and adapted to control the laser, an articulating arm adapted to support the probe, adapted to perform a systematic scan, and further adapted to be positioned by signals from the computing device, where the probe is configured to indicate a point source of radiation embedded in a person when the computing device determines the radiation signal with the highest value, and in response sends a signal to position the articulating arm where the probe is aligned with the radiation signal with the highest value, and controls the laser to indicate the embedded point source of radiation.

A further aspect of the invention is a method for locating a point source of radiation in a suspected area by providing a highly directional radiation probe with a lead pinhole collimator, a radiation detector aligned with the pinhole and a laser positioned in the probe and aligned to project a beam through the pinhole in the collimator where the laser is configured to indicate a point source of radiation detected by the radiation detector, scanning the suspected area with the radiation probe, orienting the radiation probe in the position of highest radiation detected by the radiation detector, and observing the position of the laser beam projected on the area.

Another aspect of the invention is a method of mounting a camera on the radiation probe and aligned with the laser, and photographing the position of the laser beam projected on the area.

A further aspect of the invention is a method of mounting a range finder on the radiation probe and aligned with said laser, and measuring the distance of the position of the laser beam projected on the area.

A still further aspect of the invention is a method for locating a point source of radiation in a victim using a highly directional radiation probe with a lead pinhole collimator, radiation detector and a laser diode to scan the exterior of a victim having an embedded radiation source with the radiation probe and observing the position of the laser beam projected on the victim.

Another embodiment of the invention is a method of performing a systematic scan for gamma radiation emitted from a radiation source embedded in a person that comprises providing a highly directional radiation probe with a lead pinhole collimator, and a radiation detector aligned with the pinhole, providing an articulating arm adapted to support the probe and perform a systematic scan of a person, providing an output device connected to the probe and adapted to produce a visual image of radiation intensity, scanning the exterior of a person having an embedded radiation source with the radiation probe, and observing the position of the embedded radiation source on the output device.

Another aspect of a method is an articulating arm further adapted to articulate in three dimensions.

A further aspect of a method is an articulating arm further adapted to articulate robotically.

Another aspect of the invention is a method of aligning a laser guiding radiation probe by providing a highly directional radiation probe with a lead pinhole collimator, a radiation detector aligned with the pinhole and a laser supported by a sleeve with adjusting screws positioned in the probe and where the laser is adapted to project a beam through the pinhole in the collimator, providing a cylindrical tube with a calibrated target and adapted to hold the probe in a predetermined position, and activating the laser and positioning the adjusting screws until the laser projects a beam on the target.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 9. It will be appreciated that the apparatus may vary as to configuration and as to details of the parts, and that the method may vary as to the specific steps and sequence, without departing from the basic concepts as disclosed herein.

Figure 1:
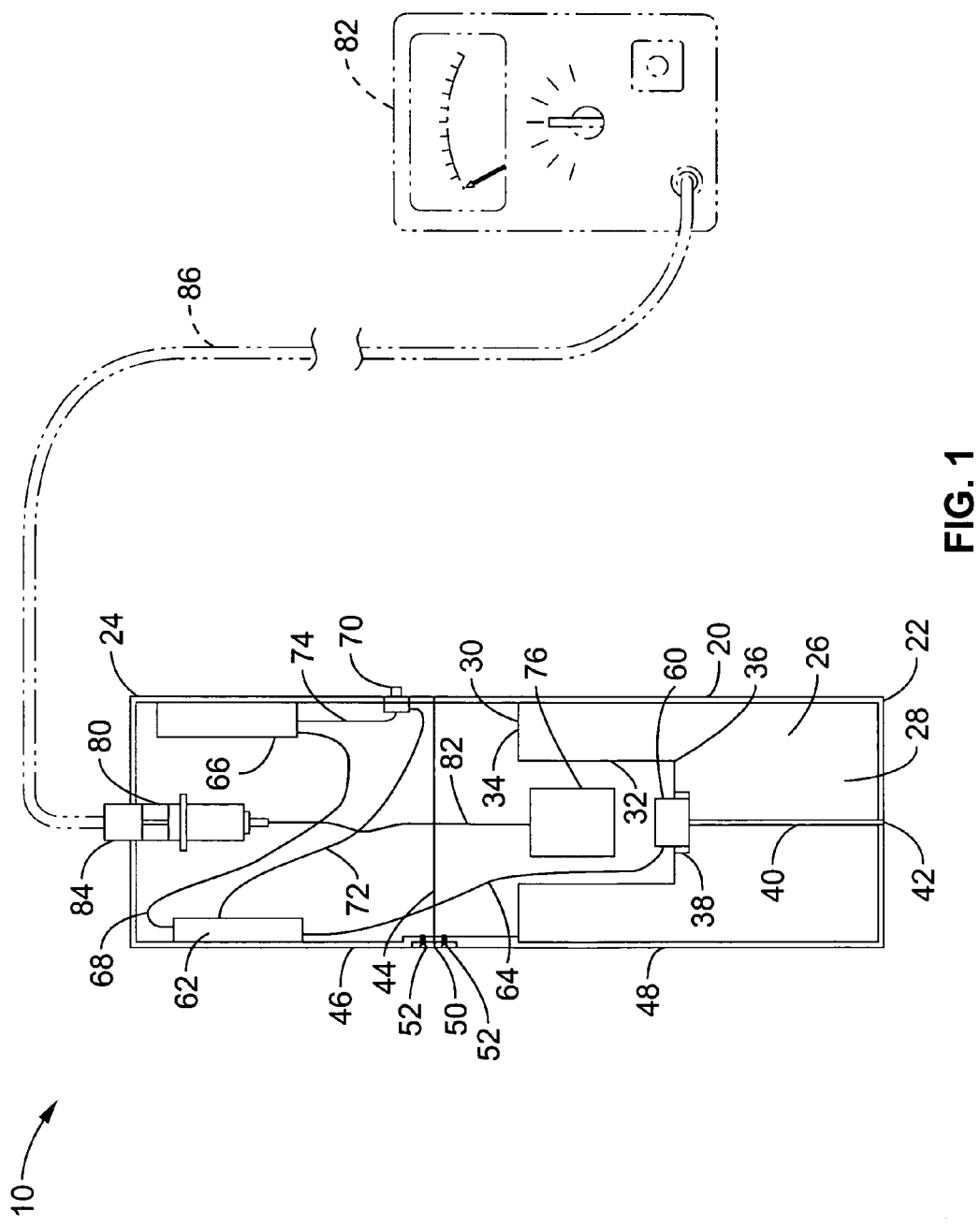
FIG. 1 is a cross section schematic view according to an embodiment of the present invention illustrating a wound probe.
Figure 2:
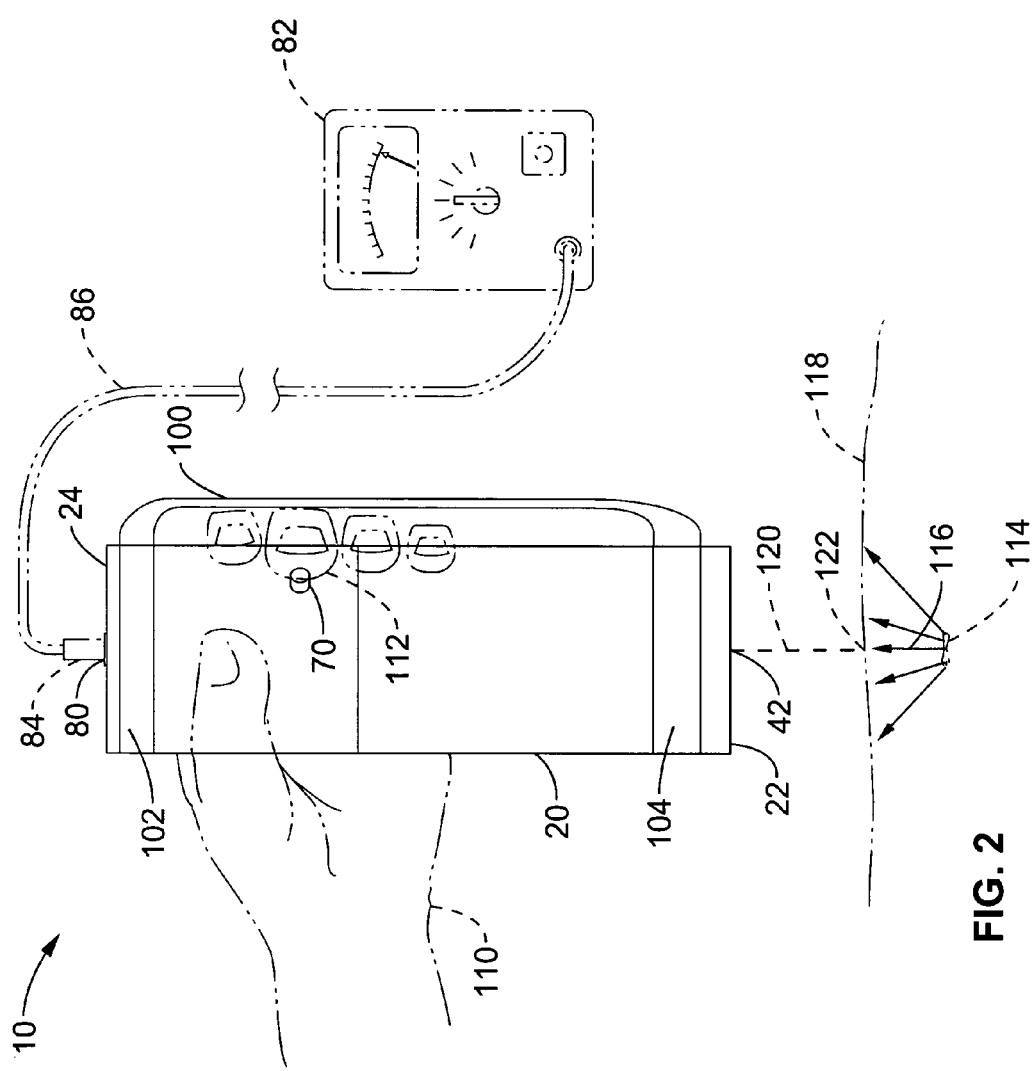
FIG. 2 is an elevation view illustrating the wound probe shown in FIG. 1 in an operation.
Figure 3:
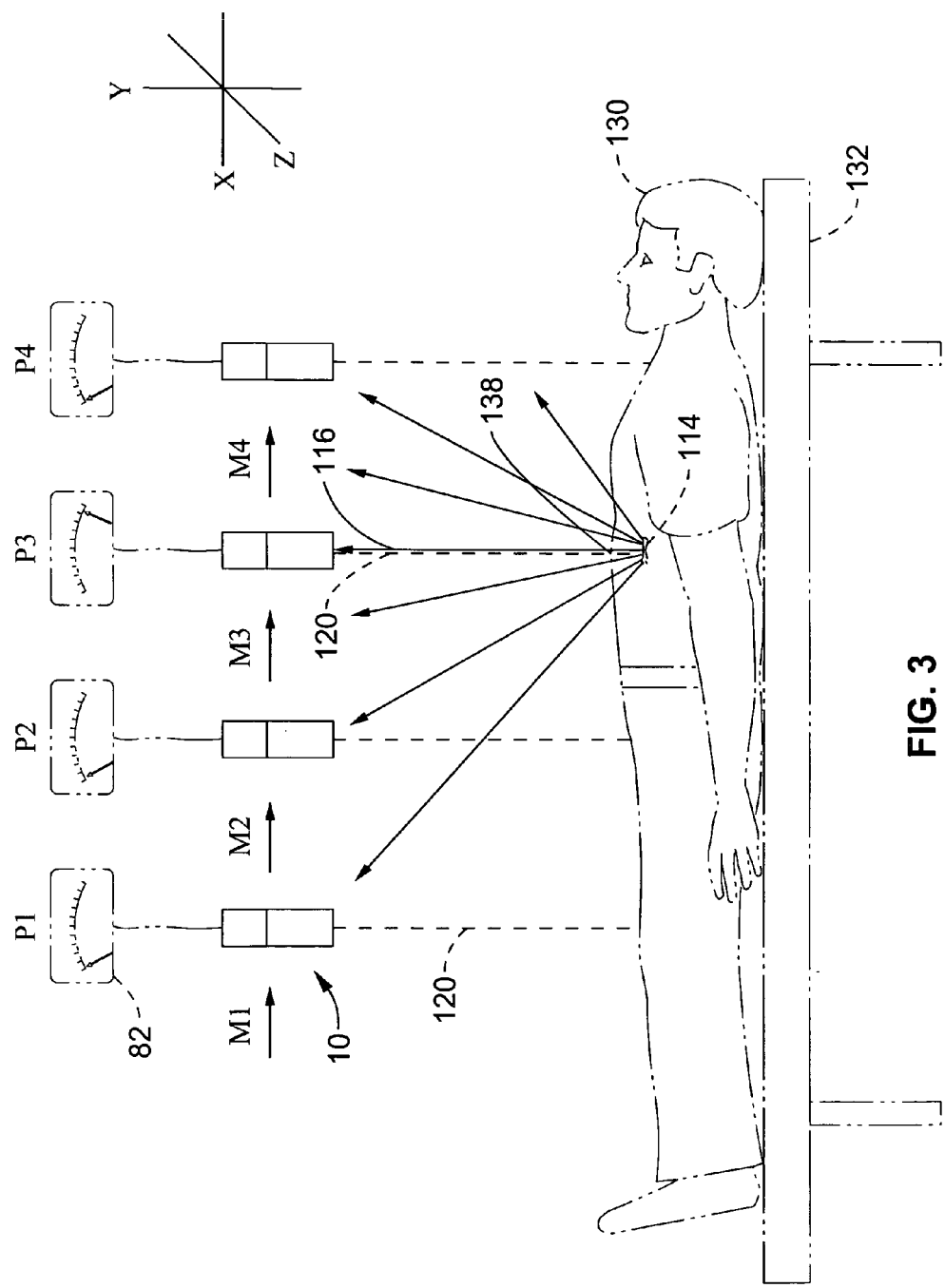
FIG. 3 is an elevation view illustrating a scanning method using the embodiment of the invention shown in FIG. 2 for pinpointing a radioactive source in a victim.

FIG. 1 through FIG. 3 illustrate an embodiment of a wound probe with a laser beam as a guide pointer, generally designated as wound probe 10.

FIG. 1 is a cross section schematic illustration of wound probe 10. Wound probe 10 has a cylindrical housing 20 with distal end 22 and proximal end 24. Housing 20 is made of a light weight durable material such as aluminum, plastic or composite material. A cylindrical lead collimator 26 is positioned in housing 20 at distal end 22. Collimator 26 has a distal end 28, and a proximal end 30. The distal end 28 of collimator 26 is aligned with the distal end 22 of housing 20. The proximal end 30 of collimator 26 has a centered, cylindrical probe recess 32 with a top end 34 and a bottom end 36. Probe recess 32 is shown with an enlarged diameter here for clarity. A laser recess 38 (shown with an enlarged diameter for clarity), is centered in the bottom end 36 of probe recess 32. A pinhole 40 is centered in collimator 26 and extends from laser recess 38 to an opening 42 at distal end 22 of housing 20. In one embodiment, collimator 26 is about 3 inches long, probe recess 32 is about 1 inch deep, and pinhole 40 is about 3 mm in diameter.

In one embodiment, housing 20 is split at line 44 with an upper half 46 and a lower half 48 for access to internal parts. A plurality of brackets 50 (one shown for clarity), couples each half 46, 48 with fasteners such as screws 52.

A laser diode 60 is mounted in laser recess 38 and oriented to produce a collimated laser beam through pinhole 40. In other embodiments, laser diode 60 can be an Argon laser, a Helium Neon laser or any collimated beam generator that produced an observable beam, such as a light beam. Laser diode 60 is electrically connected to power supply 62 through wires 64. Wires are shown schematically as a single line for clarity but may consist of one or more conductors and may be coax, multi-conductor or twisted pair. Power supply 62 is mounted on the inside of housing 20 and is electrically connected to battery pack 66 with wires 68, and to momentary switch 70 through wire 72. Momentary switch 70 is connected to battery pack 66 through wire 74 and is configured to complete the power circuit to power supply 62 when pressed.

A Geiger Mueller Tube (GMT) 76 is mounted in probe recess 32 of collimator 26 and is connected to jack 80 positioned in the distal end 24 of housing 20 with signal wire 82. Other radiation detectors as are known in the art, such as Ion chamber, Diode based, Sodium Iodide or Cesium Iodide detectors, may be used in other embodiments for different sensitivities, different radiation types, and different conditions. GMT 76 can be mounted with plastic, foam rubber or other material that is transparent to gamma rays. In one embodiment, probe recess 32 has a diameter slightly larger than GMT 76 and laser recess 38 has a diameter slightly larger than laser diode 60.

Laser diode 60 can be positioned between GMT 76 and pinhole 40 in this application because laser diode 60 is virtually transparent to most gamma rays. GMT 76 and laser diode 60 are activated by pressing and holding down momentary switch 70. In one mode, both GMT 76 and laser diode 60 are activated by momentary switch 70. In another mode, momentary switch 70 controls laser diode 60.

Wound probe 10 is shown connected to a Geiger counter 82 (shown in phantom), through jack plug 84 and signal cable 86. Other radiation indicators and analyzers as are known in the art may be used. Additionally, Geiger counter 82 may be configured to provide visual, illumination and/or audio indications of radiation intensity or signals to a computer, plotter or display device.

In another embodiment, (not shown), laser diode 60 is coupled to collimator 26 and aligned parallel to pinhole 40. In one mode, laser diode 60 emits a beam through a second pinhole (not shown). In another mode of this embodiment two or more laser diodes 60 (not shown), are oriented to project a beam through two or more pinholes in collimator 26 and parallel to pinhole 40. In a further mode of this embodiment (not shown), GMT 76 is positioned adjacent to pinhole 40 and configured to detect one or more forms of radiation such as alpha, beta and gamma radiation.

FIG. 2 illustrates one use of wound probe 10 shown in FIG. 1. Wound probe 10 is shown equipped with hand strap 100 secured to housing 20 with upper and lower strap bands 102, 104 coupled to proximal and distal end 24, 22 of housing 20 respectively. Wound probe 10 is held in hand of user 110 with a finger 112 over momentary switch 70. Geiger Counter (GC) 82 is connected to wound probe 10 with signal wire 86 and jack plug 84 in jack 80.

When user 110 desires to pinpoint a radioactive HASA source 114, shown with rays of radiation designated by arrows 116, under skin 118, user 110 holds wound probe 10 over suspected area and presses momentary switch 70. Because of the narrow field of vision of pinhole 40 (see FIG. 1), through opening 42, wound probe 10 will detect a strong signal on GC 82 only when opening 42 of pinhole 40 is directly aligned with HASA source 114. Simultaneously, laser diode 60 (see FIG. 1), projects a collimated laser beam 120 that strikes skin 118 at point 122 that is directly aligned with pinhole 40 and HASA source 114.

FIG. 3 is a schematic illustration of a scanning method for pinpointing a radioactive source 114 in a victim 130. Victim 130 is placed on platform 132 and wound probe 10 is placed in a vertical orientation as represented by the Y axis. Wound probe 10 is moved along a path represented by the X axis in direction M1 to position P1. The reading on GC 82 is relatively low. Wound probe 10 continues movement in direction M2 to position P2. Even though wound probe 10 is closer to radiation source 114, the reading on GC 82 is still relatively low due to the narrow field of vision of the pinhole 40 in the collimator 26 (see FIG. 1). Wound probe 10 continues movement in direction M3 to position P3. In position P3, wound probe 10 is aligned with radiation source 114 and radiation ray 116 will enter pinhole 40 of collimator 26 and a high reading of radiation will register on GC 82. Laser beam 120 (shown adjacent to radiation ray 116 for clarity), will strike victim 130 at point 138 to pinpoint the location of radiation source 114 on a vertical axis. Wound probe 10 continues movement in direction M4 to position P4. At position P4, the reading on GC 82 will be relatively low since radiation source 114 is no longer aligned with the pinhole 40 in wound probe 10. The scan can be repeated to precisely locate radiation source 114 embedded in victim 130. By holding wound probe 10 on a vertical axis and scanning over victim 130, the HASA source 114 can be pinpointed and marked for surgical removal at point 138. Scanning with wound probe 10 oriented in each of the X-Z, Y-Z, and X-Y planes will pinpoint position and depth of HASA source 114 in victim 130.

In another embodiment (not shown), wound probe 10 is mounted on an articulating arm to scan victim 130 and map positions of HASA sources 114. This embodiment has the advantage of reducing exposure risk to medical personnel during the scan. In one mode of this embodiment, the arm is positioned robotically and results of a systematic three dimensional scan are presented on a display or a 3D plotter. In another mode, (not shown), the diameter or cross section configuration of the pinhole 40 in wound probe 10 is changed with a sleeve insert. In a further mode (not shown) the diameter of the pinhole 40 in wound probe 10 is changed with a variable aperture mechanism. In a still further mode, two wound probes 10 with different pinhole configurations or diameters are used on the robotic articulating arm to provide both a quick general scan with the larger pinhole and a localized pinpoint scan with the smaller pinhole. In a further mode, laser 60 is not present in wound probe 10 when used with a display, plotter or printer. In a still further mode (not shown), wound probe 10 is aligned robotically with HASA source 114 and laser 60 is operated automatically. In another mode (not shown), wound probe 10 is mounted on a manual articulating arm, such as a pantograph, for scanning, mapping and indicating the location of HASA source 114.

In a further embodiment (not shown), wound probe 10 is supported on an articulating arm manipulated by a computing device that performs a systematic scan, determines the highest radiation intensity detected by wound probe 10, and controls laser 60. The computing device repositions wound probe 10 with the articulating arm until aligned with the highest radiation intensity reading and activates laser 60 to indicate the location. In another mode of this embodiment (not shown), a recording rangefinder, such as with a time of flight detector, is mounted on the articulating arm with wound probe 10 and connected to the computing device to map the topography of victim 130.

Wound probe 10 can also be used to locate HASA sources from a distance (not shown), by scanning the suspected area with wound probe 10 and observing the position of laser beam 120 in the suspected area when the highest reading occurs. Examples are pinpointing small radioactive HASA sources in a structure, accident scene or a localized area within a radius up to about 20 meters. In a further embodiment (not shown), a camera is mounted on wound probe 10 and aligned with laser beam 120 to provide a photographic image of the location of the HASA source.

Figure 4:
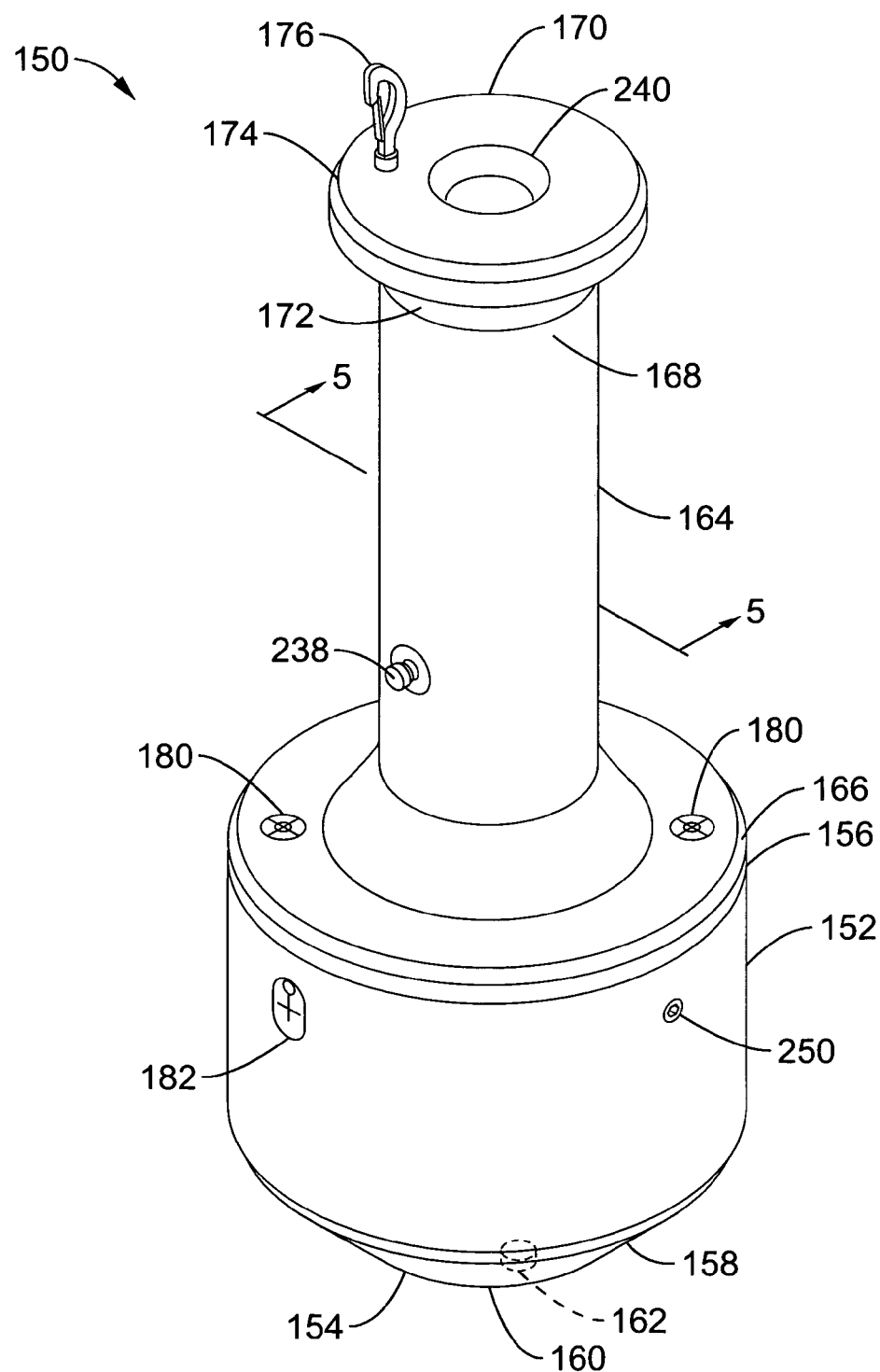
FIG. 4 is a perspective view illustrating another embodiment of a wound probe according to the present invention.
Figure 5:
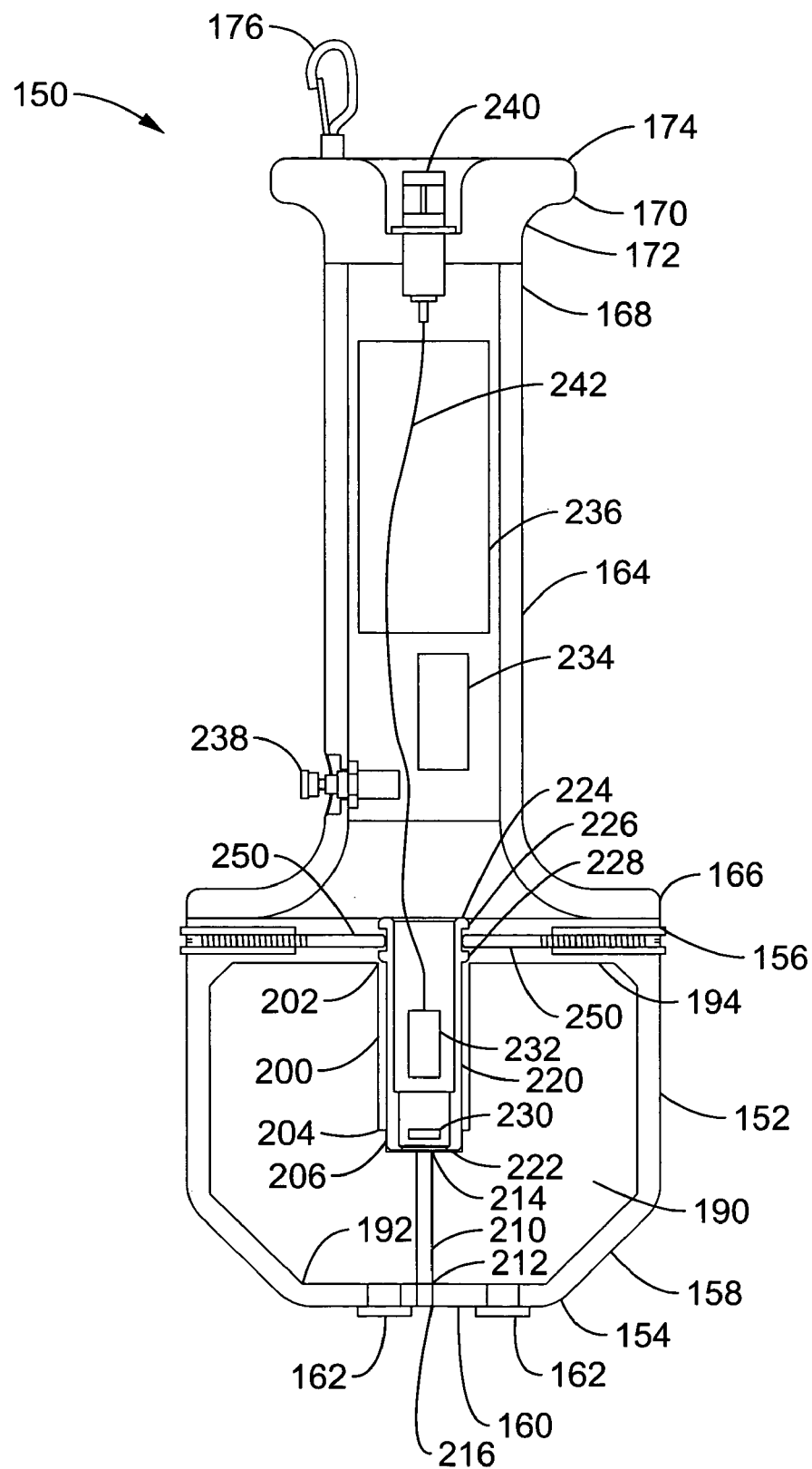
FIG. 5 is a cross-section schematic view of the embodiment of a wound probe shown in FIG. 4 and taken at line 5—5.

FIG. 4 through FIG. 8 illustrate another embodiment of a wound probe with FIG. 4 illustrating a perspective view and FIG. 5 illustrating a cross-section view taken at line 5—5 in FIG. 4.

FIG. 4 and FIG. 5 illustrate a portable wound probe generally designated as wound probe 150. Wound probe 150 has a cylindrical encasement housing 152 with a distal end 154 and a proximal end 156. In this embodiment, the distal end 154 of encasement housing 152 has a truncated cone shape with beveled surface 158 and a distal surface 160 at distal end 154 and perpendicular to the cylinder of encasement housing 152. Flexible pads 162 (shown in phantom in FIG. 4) are mounted on the distal surface 160 to prevent contamination of distal surface 160 and to prevent marring of surfaces when wound probe 150 is set down on distal surface 160. An elongated cylindrical handle 164 has a distal end 166 shaped as a circular flange base that mates with proximal end 156 of encasement housing 152, and a cylindrical proximal end 168. In one embodiment, handle 164 and encasement housing 152 are components of a probe housing. In another embodiment, the surface of cylindrical handle 164 is knurled for improved gripping. In a further embodiment, distal end 166 of handle 164 is manufactured as a separate flange and coupled to handle 164. A circular handle top 170 has distal end 172 and a proximal end 174 with proximal end 174 flaring out to a rounded knob. Distal end 172 of handle top 170 is configured to mate with proximal end 168 of handle 164. A lanyard clip 176 is positioned on proximal end 174 of handle top 170. Encasement housing 152 is typically made from aluminum, plastic or other lightweight, durable material. Handle 164 and handle top 170 are made of the same or similar lightweight durable materials.

In a preferred embodiment, encasement housing 152 is about 3.875 inches outside diameter and about 3.25 inches long, handle 164 is about 1.625 inches outside diameter and about 5.5 inches long with distal end 164 about 3.875 inches diameter, and handle top 170 is about 2.5 inches diameter at proximal end 174 and about 0.625 inches long. The walls of encasement housing 152 are about one-half inches thick while the walls of handle 164 are about one eighth inch thick. In this preferred embodiment, encasement housing 152, handle 164 and handle top 170 are made from aluminum.

A plurality of bubble levels 180 are positioned on distal flange base 166 of handle 164 to indicate when wound prove 150 is oriented in a vertical position. One or more bubble levels 182 are positioned on encasement housing 152 to indicate the horizontal orientation of wound probe 150.

Referring now to FIG. 5, encasement housing 152 encloses lead collimator 190 with distal end 192 adjoining distal end 154 of encasement housing 152 and a proximal end 194 near proximal end 156 of encasement housing 152. Collimator 190 can be poured and cast into encasement housing 152 or formed separately and inserted into encasement housing 152. The proximal end 194 of collimator 190 has a centered, cylindrical probe recess 200 with a top end 202 and a bottom end 204. In a preferred embodiment, probe recess 200 is about 2 inches long and about 0.750 inches in diameter. A centered laser recess 206 about 0.188 inches long and about 0.630 inches in diameter is centered at the bottom end 204 of probe recess 200. A pinhole bore 210 with distal opening 212 and proximal opening 214 is positioned centrally in collimator 190 and extends from laser recess 206 to a distal end 192 of collimator 190. Distal opening 212 mates with an aperture 216 in the center of distal surface 160 of encasement housing 152. In a preferred embodiment, pinhole bore 210 and aperture 216 are about 0.187 inches in diameter. In another embodiment, pinhole bore 210 and aperture 216 are about 0.118 inches in diameter. In a further embodiment, a removable sleeve (not shown), is inserted in pinhole bore 210 to change the diameter or cross section configuration. In another embodiment, (not shown), collimator 190 is formed as a cylindrical center core with pinhole bore 210 and a cylindrical shell around the center core where the cylindrical shell can be removed from encasement housing 152 to reduce the thickness and weight of the lead shielding when lower energy radiation is encountered.

A cylindrical probe sleeve 220 (see also FIG. 7), is configured to insert into probe recess 200. Probe sleeve 220 has a distal end 222 and a proximal end 224. Distal end 222 is open and has an outer diameter slightly smaller than laser recess 206. Proximal end 224 is open and has a raised lip 226 and a raised ridge 228 around the outer circumference of cylindrical probe 220. In a preferred embodiment, probe sleeve 220 is about 2 inches long and raised ridge 228 is spaced apart from lip 226 by about 0.188 inches. Distal end 222 of probe sleeve 220 has an inner diameter of about 0.422 inches that extends proximally about 0.465 inches. The remainder of probe sleeve 220 has an inner diameter of about 0.500 inches. Probe sleeve 220 is inserted in probe recess 200 so that distal end 222 fits snugly in laser recess 206.

A laser diode 230 is positioned in probe sleeve 220 at distal end 222 and a GMT detector 232 is positioned in about the middle of probe sleeve 220. Laser diode 230 and GMT 232 are electrically connected to power supply 234, battery pack 236 and momentary switch 238 mounted in handle 164 as previously shown in FIG. 4. Momentary switch 238 is positioned near the distal end 166 of handle 164 as also shown in FIG. 4. Electrical connections are configured similar to those described in FIG. 1 and have been omitted here for clarity.

GMT 232 is connected to jack 240 through cable 242. Jack 240 is positioned at the proximal end 174 of handle top 170 as also shown in FIG. 4.

Figure 9:
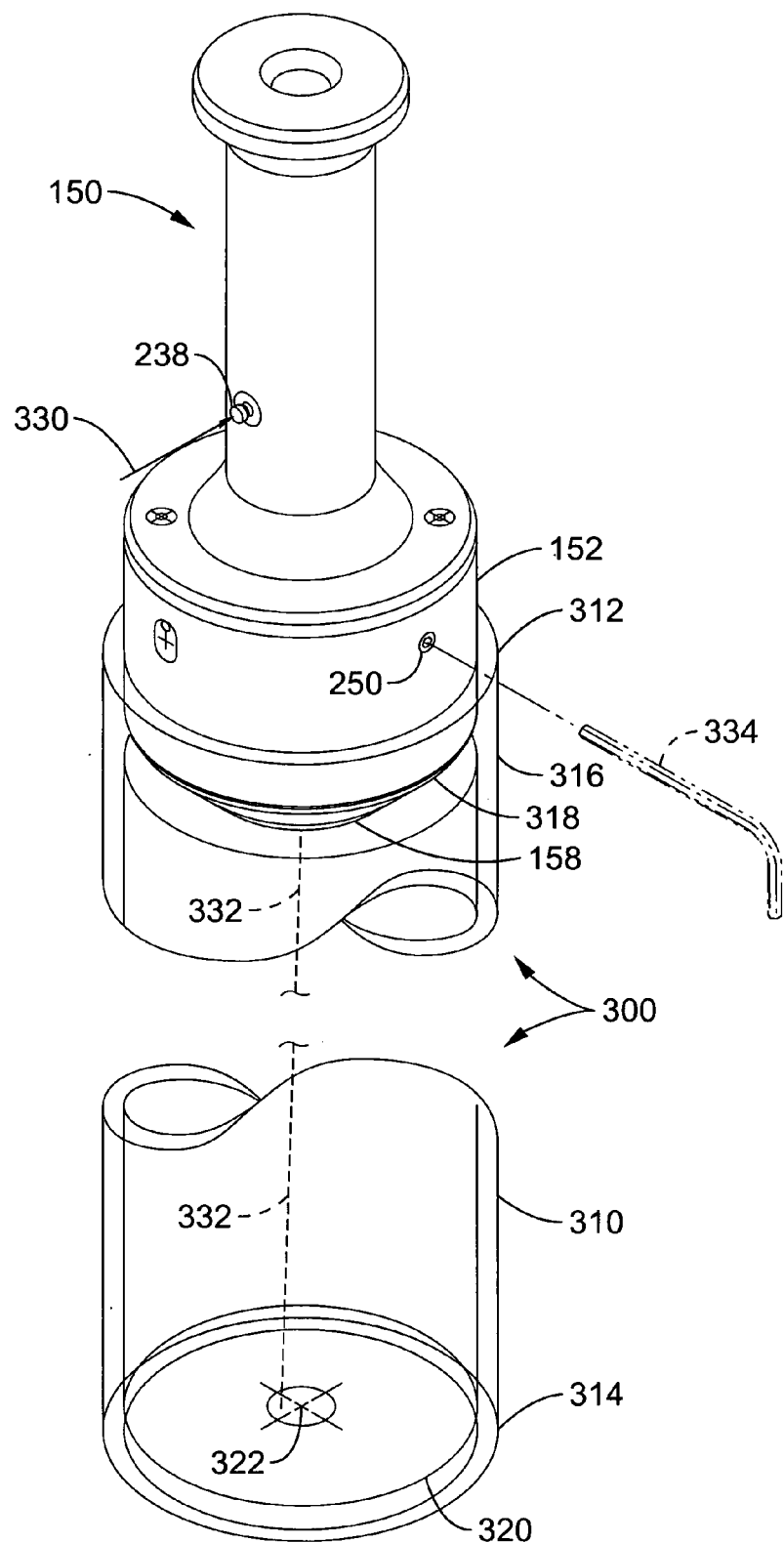
FIG. 9 is a perspective view of a wound probe as shown in FIG. 4 and a calibration device and method for adjusting the alignment of the laser.

Adjustment screws 250 are positioned near the proximal end 156 of encasement housing 152 as also shown in FIG. 4, and are configured to contact probe sleeve 220 between lip 226 and raised ridge 228 at proximal end 224. Adjustment screws 250 reposition proximal end 224 of probe sleeve 220 and thus reorient laser diode 230 to align precisely with pinhole bore 210. A method for aligning laser diode 230 is shown in FIG. 9. As discussed previously in FIG. 3, wound probe 150 can be used to locate HASA sources in a localized area up to about a 20 meter radius or further, depending on the level of radiation exposure encountered.

Figure 6:
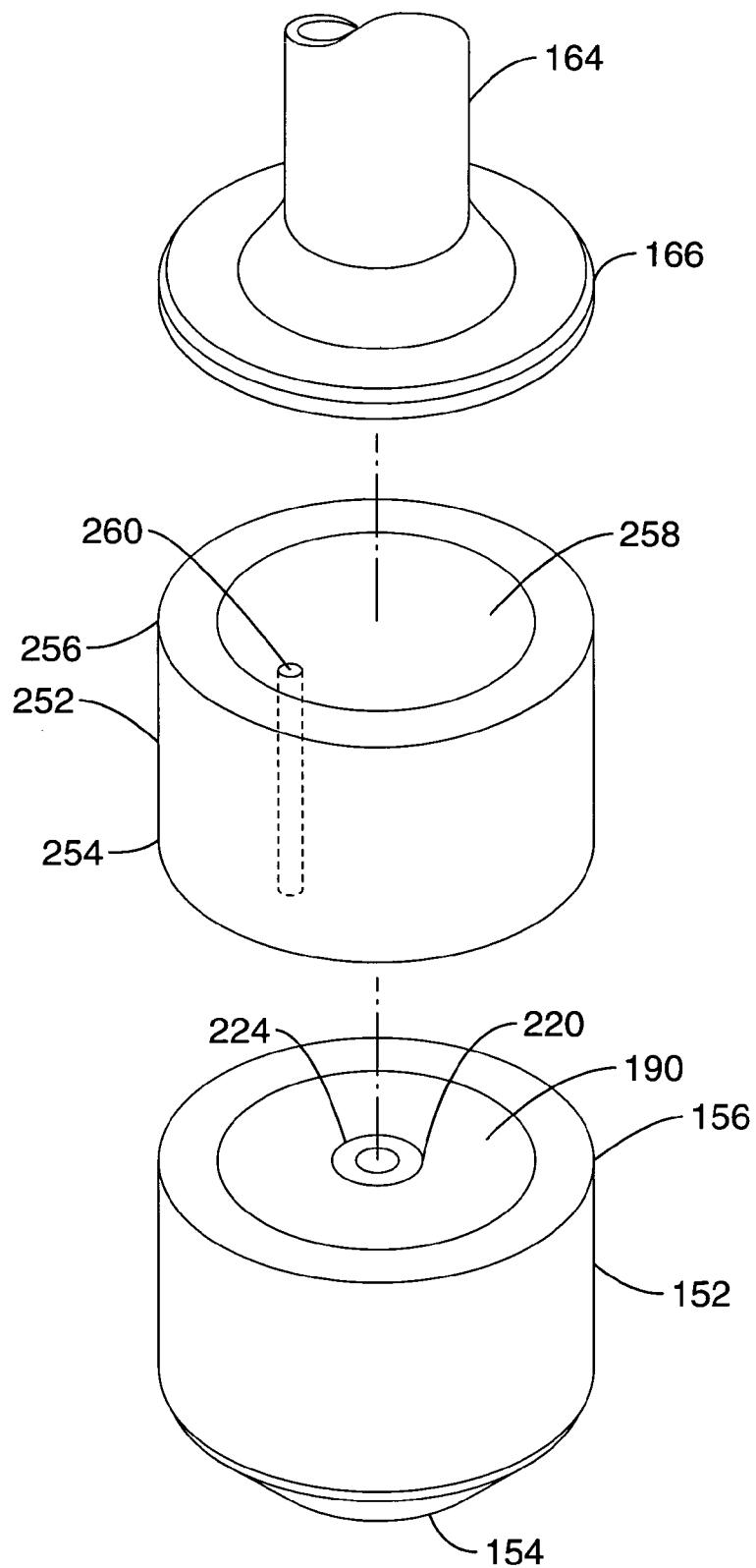
FIG. 6 is an exploded view of the wound probe shown in FIG. 4 and FIG. 5 illustrating the insertion of a lead back plug for area scans.

FIG. 6 illustrates an exploded view of a cylindrical lead filled plug, designated as 252, with distal end 254 and proximal end 256, positioned at the proximal end 156 of encasement housing 152. Plug 252 is used when it is desired to conduct area scans with wound probe 150 (shown in FIG. 4 and FIG. 5). Plug 252 has a lead core 258 and in one embodiment, lead core 258 is about the same axial length and diameter as lead collimator 190 shown in FIG. 5. The position of lead core 258 shields or blocks radiation sources located behind the probe from registering on GMT 232 (see FIG. 5), such as during a horizontal area scan. An access hole 260 is shown off-center in lead core 258 for wires to the GMT 232 and laser 230 as described previously in FIG. 5. Hole 260 is oriented away from the center axis of lead core 258 to prevent radiation from penetrating into proximal end 224 of probe sleeve 220 through hole 260.

In a preferred embodiment (not shown), wires are embedded off-center in lead core 258 with quick connectors or mating jack connectors at each end. Wires may also be routed in the shell of plug 252 or on the exterior of plug 252. The shell of plug 252 is made of similar material as encasement housing 152. Distal end 254 of plug 252 mates with proximal end 156 of encasement 152. Proximal end 256 of plug 252 mates with distal end 166 of handle 164. In another embodiment (not shown), plug 252 has quick connect fasteners, such as clips or a twist lock, for mating with encasement housing 152 and handle 164. In further embodiment (not shown), plug 252 has a handle or grip for carrying in a horizontal orientation. In another embodiment (not shown), a range finder or camera is attached to the outside of plug 252.

Figure 7:
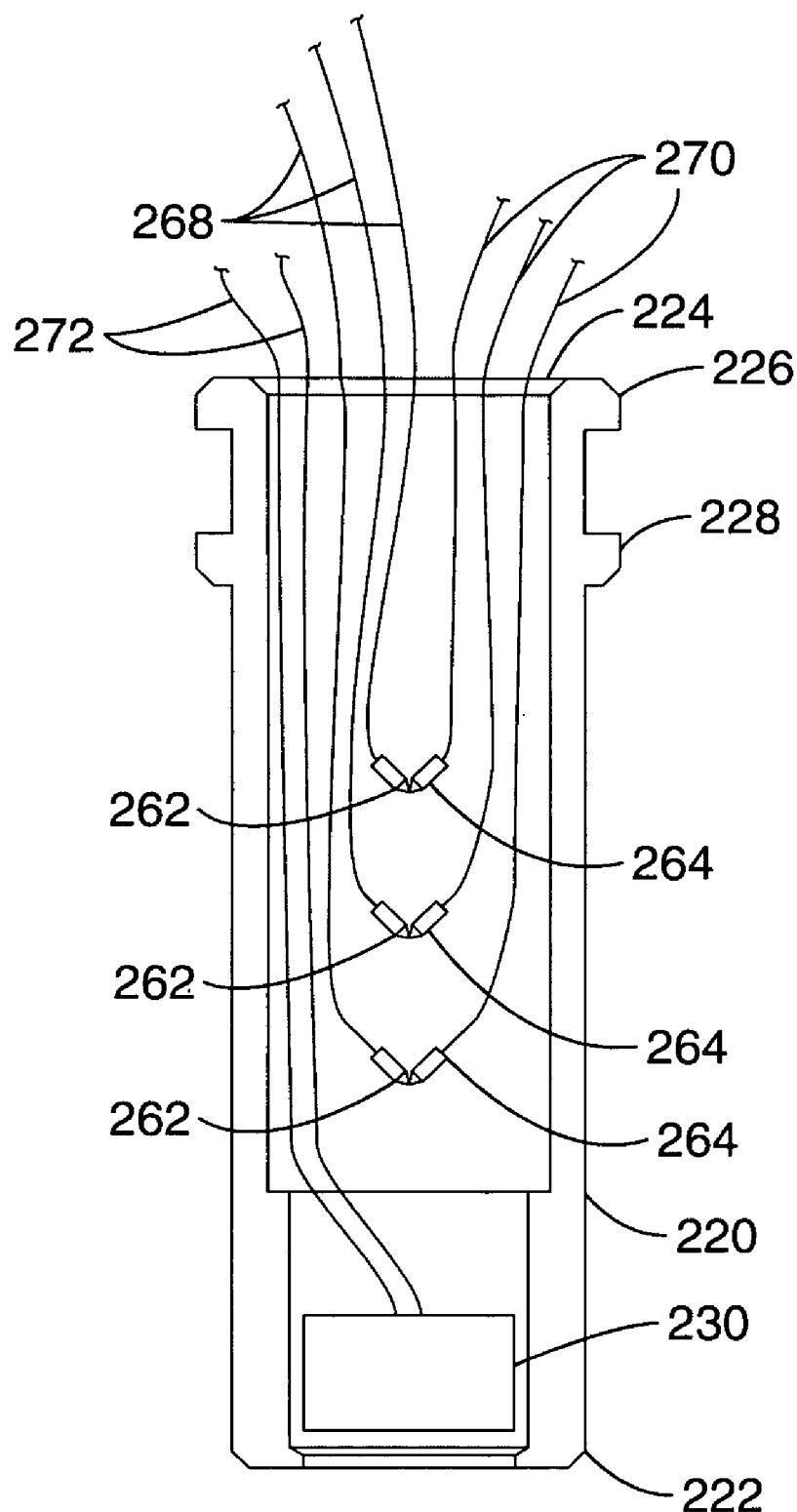
FIG. 7 is a detailed cross section view of another embodiment of a probe sleeve for a wound probe as previously shown in FIG. 5 and illustrated with multiple radiation detectors.

FIG. 7 illustrates a cross section of a probe sleeve 220 for another embodiment of a wound probe 150 as previously shown in FIG. 5. As discussed previously, laser diode 230 is positioned in distal end 222 of probe sleeve 220. A plurality of radiation detectors, designated here as left detectors 262, and right detectors 264 are positioned in a stacked configuration along the center axis of probe sleeve 220. In one embodiment, radiation detectors 262, 264 are omni-directional. Left detectors 262 are connected to signal wires 268 and right detectors 263 are connected to signal wires 270. In one mode, signals wires 268 for left detectors 262 are switched off (switch not shown), so that radiation is only detected by right detectors 264 and communicated through signal wires 270 to reduce probe sensitivity. Detectors 262, 264 can be oriented in different configurations, switched in different configurations and/or consist of different types of detectors depending on radiation types detected, the sensitivity ranges desired, needs of the user, or the situation encountered. Detectors 262, 264 are typically lightweight and can be mounted in foam rubber, plastic (not shown), or similar low density material that is transparent to gamma rays. Power wires 272 to laser diode 230 are routed through probe sleeve 220 without interfering with detection of gamma rays by detectors 262, 264. In other embodiments, laser diode 230 can be any source that generates an observable collimated beam including an Argon laser or a Helium Neon laser. In further contemplated embodiments, a light source or infrared source may be used to generate an observable beam. In another embodiment (not shown), laser diode 230 is positioned in another location and detectors 262, 264 are aligned with pinhole bore 210 without obstruction to detect different forms of radiation. In one mode (not shown), laser diode 230 is projected through a bore parallel to pinhole bore 210. In another mode (not shown), one or more laser diodes 230 are mounted on the proximal end 194 of collimator 190 and projected through one or more parallel bores in collimator 190. In a further mode (not shown), each laser diode 230 is mounted in a sleeve similar to probe sleeve 220.

Figure 8:
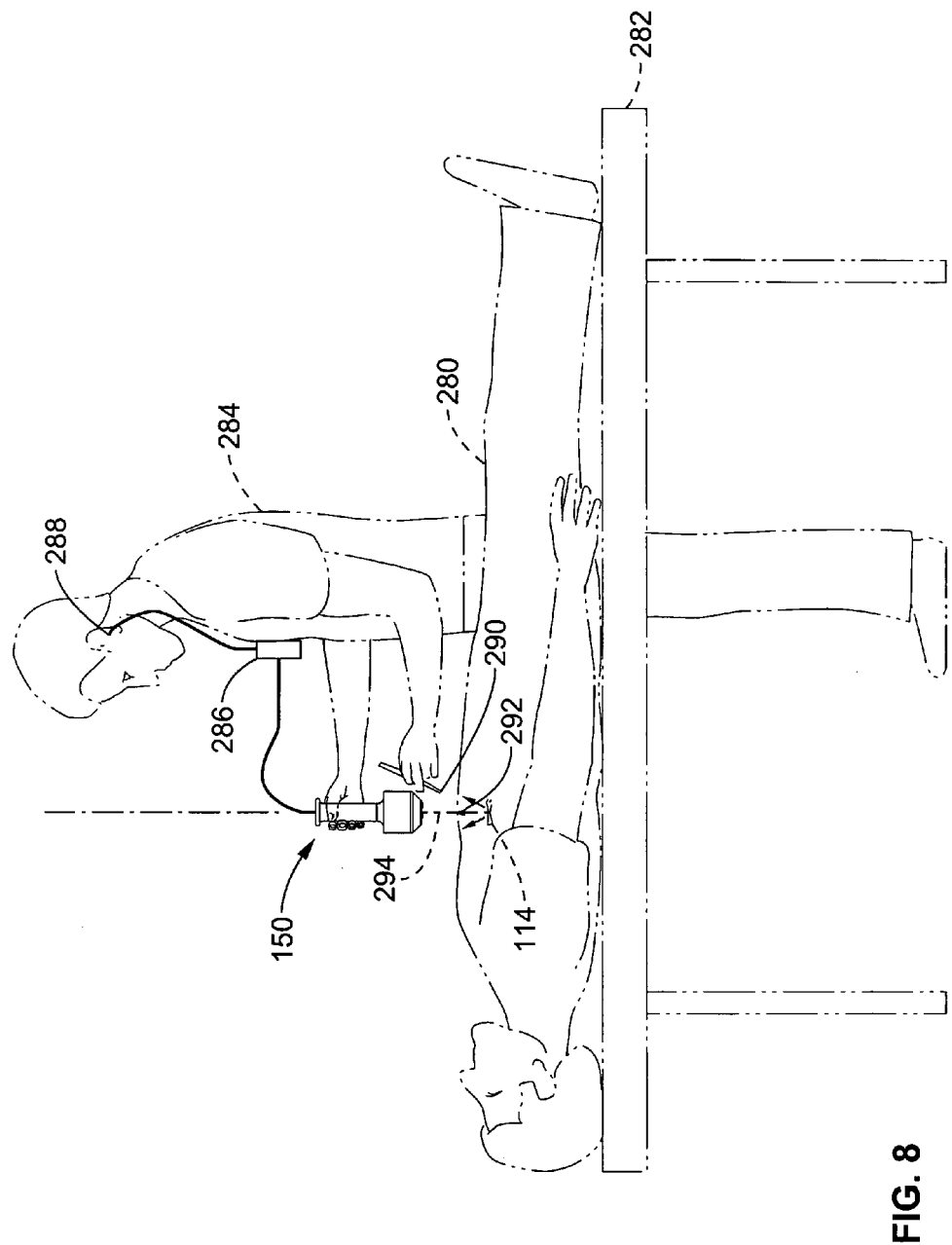
FIG. 8 is an elevation view illustrating a method of using an embodiment of a wound probe as previously shown in FIG. 4 on a patient with an embedded radiation source.

FIG. 8 illustrates a method of using a wound probe 150 with a patient 280 on an operating table 282 with an embedded radiation source 114. A wound probe 150 (as previously shown in FIG. 4 and FIG. 5), is held over the patient for scanning (as described in FIG. 3), by physician 284. Wound probe 150 is connected to a hands free radiation counter 286 (Geiger Counter) that produces different audio tones based on radiation intensity detected and transmits audio signals to physician 284 through earpiece 288. Physician 284 (or any trained person) can quickly indicate the position of radiation source 114 by making a mark with marker 290 at point 292 indicated by laser beam 294 when the highest radiation intensity is audibly detected.

Wound probe 150 can also be mounted on an articulating arm (not shown) to provide a systematic or robotic scan with output to a visual display device such as a display screen, printer, plotter or stereotactic device such as a CT or MRI. The articulating arm can also be configured to robotically align wound probe 150 with the highest intensity HASA radiation detected and indicate the position with laser beam 294 as discussed previously in FIG. 3.

FIG. 9 illustrates a calibration cylinder 300 adapted to calibrate the alignment of the laser beam from wound probe 150. Calibration cylinder 300 is a tube 310 with distal end 312, proximal end 314 and near distal position 316. Tube 310 is made of a transparent material such as Lexan, Acrylic or glass and has an inside diameter slightly larger than the outside diameter of encasement housing 152 on wound probe 150. A beveled inner collar 318 is positioned inside tube 310 at position 316 and is adapted to mate with beveled surface 158 of collimator housing 152. The beveled inner collar 318 is positioned perpendicular to tube 310 and parallel to bottom surface 320 mounted at proximal end 314 of tube 310. Bottom surface 320 has crosshair target 322 as an aim point.

Momentary switch 238 on wound probe 150 is activated as shown by arrow 330 that could be a finger or other means such as a trigger cable. Laser beam 332 is projected onto bottom surface 320. A hex wrench 334 is used to position adjustment screw(s) 250 on wound probe 150 until laser beam 332 is in the center of cross hairs 322.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A probe apparatus for locating a source of radioactivity, comprising:
   a collimator;
   said collimator having proximal and distal ends;
   said collimator having a pinhole positioned in said distal end;
   a radiation detector positioned adjacent said pinhole; and
   a light source positioned adjacent said pinhole;
   wherein said collimator and said radiation detector form a highly directional probe for detecting radioactivity;
   wherein said collimator and said light source form a highly directional light emitter for visually locating said source of radioactivity; and
   a sleeve configured to mount within said collimator;
   said sleeve adapted to support said light source;
   said sleeve further adapted to adjustably align said light source with said pinhole.

2. An apparatus as recited in claim 1, wherein said radiation detector comprises a gamma radiation detector.

3. An apparatus as recited in claim 2, wherein said gamma radiation detector is selected from the group consisting essentially of an Ion Chamber, a Geiger Mueller Tube, a Diode Based Detector, a Sodium Iodide detector and a Cesium Iodide detector.

4. An apparatus as recited in claim 1, wherein said light source is selected from the group consisting essentially of a laser diode, an Argon laser, and a Helium Neon laser.

5. An apparatus as recited in claim 1, further comprising a housing adapted to support said collimator.

6. An apparatus as recited in claim 5, further comprising a switch adapted to activate said light source means for generating an observable beam, said switch positioned on said housing.

7. An apparatus as recited in claim 6, wherein said housing is constructed of aluminum.

8. An apparatus as recited in claim 5, further comprising a battery pack configured to provide power to said light source, said battery pack positioned in said housing.

9. An apparatus as recited in claim 5, further comprising a plurality of level indicators associated with said housing, said level indicators configured to indicate orientation of said apparatus.

10. An apparatus as recited in claim 5, further comprising:
    a lead plug having a distal end and a proximal end;
    said distal end of said plug adapted to couple to said proximal end of said collimator;
    said proximal end of said plug adapted to couple to said housing;
    wherein said plug is adapted to block said radiation detector from gamma radiation.

11. An apparatus as recited in claim 1, wherein said pinhole has a diameter of up to approximately 0.250 inches.

12. An apparatus as recited in claim 11, further comprising a removable sleeve adapted to change the cross section area of said pinhole.

13. An apparatus as recited in claim 11, further comprising a variable aperture mechanism adapted to change the diameter of said pinhole.

14. An apparatus as recited in claim 1, wherein said collimator comprises:
    a center core; and
    a cylindrical shell, said shell adapted to mate with said center core;
    wherein said shell is adapted to be removable from said probe apparatus.

15. An apparatus as recited in claim 1, wherein said apparatus is adapted to be coupled to a visual and/or audible indicator of radiation intensity.

16. An apparatus as recited in claim 1, further comprising:
an articulating support arm adapted for performing a systematic scan; and
a visual display device coupled to said radiation detector;
wherein said visual display device is configured to produce a visual image of radiation intensity detected by said radiation detector when a systematic scan is performed.

17. An apparatus as recited in claim 16, wherein said visual display device is selected from the group consisting essentially of a printer, a plotter, a video display screen, and a stereotactic device.

18. An apparatus as recited in claim 16, wherein said articulating support arm is further adapted to articulate in three dimensions.

19. An apparatus as recited in claim 16, wherein said articulating support arm is further adapted to articulate robotically.

20. A probe for indicating a source of radioactivity, comprising:
a lead collimator having proximal and distal ends;
a pinhole positioned in said distal end of said collimator;
means for detecting radiation passing through said pinhole;
means for generating an observable beam through said pinhole;
wherein said collimator and said means for detecting radiation form a highly directional probe;
wherein said collimator and said means for generating an observable beam form a highly directional light emitter for visually locating said source of radioactivity; and
a sleeve configured to insert into said collimator;
said sleeve adapted to support said means for generating an observable beam;
said sleeve further adapted to adjustably align said means for generating an observable beam with said pinhole.

21. A probe as recited in claim 20, wherein said means for detecting radiation comprises a gamma radiation detector.

22. A probe as recited in claim 21, wherein said gamma radiation detector is selected from the group consisting essentially of an Ion Chamber, a Geiger Mueller Tube, a Diode Based Detector a Sodium Iodide detector and a Cesium Iodide detector.

23. A probe as recited in claim 20, wherein said means for generating an observable beam is selected from the group consisting essentially of a laser diode, an Argon laser, and a Helium Neon laser.

24. A probe as recited in claim 20, further comprising a handle adapted to support said collimator.

25. A probe as recited in claim 24, further comprising a switch adapted to activate said means for generating an observable beam, said switch positioned on said handle.

26. A probe as recited in claim 24, further comprising a battery pack configured to provide power to said means for generating an observable beam.

27. A probe as recited in claim 24, further comprising a plurality of level indicators configured to indicate orientation of said probe.

28. A probe as recited in claim 24, wherein said handle is constructed of aluminum.

29. A probe as recited in claim 24, further comprising:
a lead plug having a distal end and a proximal end;
said distal end of said plug adapted to couple to said proximal end of said collimator;
said proximal end of said plug adapted to couple to said handle;
wherein said plug is adapted to block said means for detecting radiation from gamma radiation.

30. A probe as recited in claim 20, wherein said pinhole has a diameter of up to approximately 0.250 inches.

31. A probe as recited in claim 30, further comprising a removable sleeve adapted to change the cross section area of said pinhole.

32. A probe as recited in claim 30, further comprising a variable aperture mechanism adapted to change the diameter of said pinhole.

33. An apparatus as recited in claim 20, wherein said collimator comprises:
a center core; and
a cylindrical shell, said shell adapted to mate with said center core;
said shell further adapted to be removable from said probe.

34. A probe as recited in claim 20, wherein said probe is adapted to couple to a visual and/or audible indicator of radiation intensity.

35. A probe as recited in claim 20, further comprising:
an articulating support arm adapted for performing a systematic scan; and
means for producing a visual image of radiation intensity detected by said radiation detection means when a systematic scan is performed.

36. A probe as recited in claim 35, wherein said means for producing a visual image is selected from the group consisting essentially of a printer, a plotter a display screen and a stereotactic device.

37. A probe as recited in claim 35, wherein said articulating support arm is further adapted to articulate in three dimensions.

38. A probe as recited in claim 35, wherein said articulating support arm is further adapted to articulate robotically.

39. A probe as recited in claim 20:
wherein said collimator has a single pinhole; and
wherein said means for generating an observable beam is positioned between said pinhole and said means for detecting radiation.

40. A probe as recited in claim 20, further comprising:
a housing adapted to support said collimator;
wherein said means for generating an observable beam can be adjustably aligned with said pinhole without accessing said collimator supported in said housing.

41. A probe as recited in claim 1:
wherein said collimator has a single pinhole; and
wherein said light source is positioned between said pinhole and said radiation detector.

42. A probe as recited in claim 1, further comprising:
a housing adapted to support said collimator;
wherein said light source can be adjustably aligned with said pinhole without accessing said collimator supported in said housing.

43. A probe with laser guiding for indicating a point source of gamma radiation, comprising:
a lead collimator having proximal and distal ends;
a pinhole positioned in said distal end of said collimator;
at least one gamma radiation detector positioned within said collimator to detect gamma radiation passing through said pinhole; and
a laser emitter positioned in said collimator and aligned to project a beam through said pinhole in said collimator;
wherein said collimator and said gamma radiation detector form a highly directional radiation probe;

wherein said laser emitter is configured to indicate a point source of gamma radiation detected by said gamma radiation detector; and wherein said collimator comprises:
 a center core, said center core mounted in said probe;
 a cylindrical shell, said shell adapted to mate with said center core;
 said shell further adapted to be removable from said probe.

44. A probe as recited in claim 43, wherein said gamma radiation detector is selected from the group consisting essentially of an Ion Chamber, a Geiger Mueller Tube, a Diode Based Detector, a Sodium Iodide detector and a Cesium Iodide detector.

45. A probe as recited in claim 43, wherein said laser emitter is selected from the group consisting essentially of a laser diode, an Argon laser and a Helium Neon laser.

46. A probe as recited in claim 43, further comprising a housing adapted to support said collimator.

47. A probe as recited in claim 46, further comprising a momentary switch adapted to activate said laser emitter, said switch positioned on said housing.

48. A probe as recited in claim 46, further comprising a battery pack configured to provide power to said laser emitter.

49. A probe as recited in claim 46, further comprising a plurality of level indicators configured to indicate orientation of said probe.

50. A probe as recited in claim 46, wherein said housing is constructed of aluminum.

51. A probe as recited in claim 46, further comprising:
 a lead plug having a distal end and a proximal end;
 said distal end of said plug adapted to couple to said proximal end of said collimator;
 said proximal end of said plug adapted to couple to said housing;
 wherein said plug is adapted to block gamma radiation to said gamma radiation detector.

52. A probe as recited in claim 43, wherein said pinhole has a diameter of up to approximately 0.250 inches.

53. A probe as recited in claim 52, further comprising a removable sleeve adapted to change the cross section area of said pinhole.

54. A probe as recited in claim 52, further comprising a variable aperture mechanism adapted to change the diameter of said pinhole.

55. A probe as recited in claim 43, wherein said probe is adapted to couple to a visual and/or audible indicator of radiation intensity.

56. A probe as recited in claim 43, further comprising;
a sleeve configured to mount within said collimator;
said sleeve adapted to support said laser emitter;
said sleeve further adapted to adjustably align said laser emitter with said pinhole.

57. A probe apparatus for locating a source of radioactivity, comprising:
a collimator;
a single pinhole within said collimator;
a light source mounted within said collimator;
wherein said light source is positioned adjacent said pinhole;
a radiation detector positioned adjacent said light source and aligned with said pinhole;
wherein said pinhole and said radiation detector form a highly directional probe for detecting radioactivity;
wherein said pinhole and said light source form a highly directional light emitter for visually locating said source of radioactivity; and
wherein said collimator comprises:
 a center core, said center core mounted in said probe;
 a cylindrical shell, said shell adapted to mate with said center core;
 said shell further adapted to be removable from said probe.

58. A probe as recited in claim 57, further comprising:
a housing adapted to support said collimator;
wherein said light source can be adjustably aligned with said pinhole without accessing said collimator supported in said housing.

* * * * *